United States Patent
Chien et al.

(10) Patent No.: US 9,380,223 B2
(45) Date of Patent: Jun. 28, 2016

(54) DEVICE FOR CONTACTLESSLY TESTING PASSIVE ROUTING SUBSTRATES

(71) Applicant: National Tsing Hua University, Hsinchu (TW)

(72) Inventors: Jui-Hung Chien, Taipei (TW); Hao Yu, New Taipei (TW); Ruei-Siang Hsu, Taipei (TW); Hsueh-Ju Lin, Hsinchu County (TW); Shih-Chieh Chang, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 307 days.

(21) Appl. No.: 14/101,521

(22) Filed: Dec. 10, 2013

(65) Prior Publication Data

US 2015/0103161 A1   Apr. 16, 2015

(30) Foreign Application Priority Data

Oct. 14, 2013 (TW) .............................. 102137011 A

(51) Int. Cl.
*G01N 25/72* (2006.01)
*G01N 1/00* (2006.01)
*G01R 1/00* (2006.01)
*G06T 7/00* (2006.01)
*H04N 5/33* (2006.01)

(52) U.S. Cl.
CPC ................. *H04N 5/33* (2013.01); *G01N 25/72* (2013.01); *G06T 7/001* (2013.01); *G06T 2207/10048* (2013.01); *G06T 2207/30148* (2013.01)

(58) Field of Classification Search
None
See application file for complete search history.

(56) References Cited

U.S. PATENT DOCUMENTS

| | | | | |
|---|---|---|---|---|
| 4,755,874 A | * | 7/1988 | Esrig | G01N 21/95607 348/126 |
| 5,250,809 A | * | 10/1993 | Nakata | G01R 31/048 250/330 |
| 5,309,108 A | * | 5/1994 | Maeda | G06T 7/001 324/501 |
| 6,730,912 B2 | * | 5/2004 | Sun | G01N 25/72 250/341.1 |
| 2006/0193497 A1 | * | 8/2006 | Matsumoto | G06T 7/0004 382/112 |
| 2006/0193507 A1 | * | 8/2006 | Sali | G01N 21/9501 382/145 |
| 2007/0177787 A1 | * | 8/2007 | Maeda | G06T 7/001 382/141 |
| 2011/0235017 A1 | * | 9/2011 | Iwasaki | H04N 5/2354 356/4.01 |
| 2012/0091340 A1 | * | 4/2012 | Young | H04N 5/33 250/332 |

* cited by examiner

*Primary Examiner* — Reza Aghevli
(74) *Attorney, Agent, or Firm* — Jackson IPG PLLC; Demian K. Jackson

(57) ABSTRACT

A device for fault detecting passive routing substrates. Thermal behavior differences before and after a passive routing substrate is damaged are used. A batch of passive routing substrates is fault detected without running a functional test. In addition, the passive routing substrates are not contacted and are not damaged on detection. The device provides superior and precise detection before stacking the passive routing substrates.

2 Claims, 3 Drawing Sheets

DEVICE FOR CONTACTLESSLY TESTING PASSIVE ROUTING SUBSTRATES

This application claims the priority benefits under 35 U.S.C. 119(a)-(d) or (f) of Taiwanese Patent Application 1 021 3701 1 filed Oct. 14, 2013.

TECHNICAL FIELD OF THE INVENTION

The present invention relates to detecting passive routing substrates and more particularly, relates to using thermal behavior differences before and after a passive routing substrate is damaged to detect passive routing substrates without contacting the substrates, where the passive routing substrates are heated up and their thermal images are captured to obtain thermal behavior differences in between for finding out good passive routing substrates before stacking them with superior and precise detection.

DESCRIPTION OF THE RELATED ARTS

Stacked chips use passive routing substrates as a medium for inter-chip signal transmission; hence, the yield of the passive routing substrates affects product cost of the stacked chips greatly.

General tests for stacked chips include pre-stacking tests and post-stacking tests. The pre-stacking tests separately detect components including a few chips, passive routing substrates and substrates before stacking; and, the post-stacking tests detect the components after stacking. If damaged passive routing substrates are not found through detection before stacking and the damaged passive routing substrates are still stacked into finished chip products, extra cost of other good components are apparently paid with increased cost of production although the post-stacking tests can tell good stacked chips from bad ones.

Hence, for saving cost of follow-up processes and tests, testing the passive routing substrates before stacking is necessary. Traditional passive routing substrate tests use contacting probes to conduct currents to metal wires on surfaces of the passive routing substrates for judging damage by observing current behaviors. For example, in the U.S. Pat. No. 7,863,106, a probe and a glass plate are installed on the passive routing substrates for testing with electricity. Yet, the use of the probe will cause broken passive routing substrates. Besides, in the U.S. Patent No. 2011/0170572, a plurality of thin-film gaskets are wound around a permeable pipe for circulating heat of a compressed gas between the permeable pipe and the thin-film gaskets to thereby heating or cooling the thin-film gaskets. Then, temperature calculation is done with the heat distribution of the winding surface and the normal samples. If temperature difference appears, the layer of the thin-film gaskets is damaged. However, the temperature difference is not suitable to be used on directly judging fineness of the unknown passive routing substrates because they are micron-level components and there may be still some error between them even in the same batch. Besides, for every batch of passive routing substrates, the design of metal wires may differ greatly, and, furthermore, no standard sample for comparison can be found for verifying the accuracy of the passive routing substrate tests. In the U.S. Pat. No. 6,730,912, a body is heated up at an end and an infrared-ray camera is used to record lateral heat transfer behavior. Then, a maximum temperature value is calculated out through image differential to find out a normal or angled crack. However, although image differential is used, it only works for passive routing substrates made of a single material or compound and requires a known good passive routing substrate for comparison, which is not simple. However, another prior art is presented, where, after known-normal and known-abnormal electronic components are heated up through conducting electricity, a weighting table is built for temperature difference and the table is used to analyze whether unknown electronic components are normal or not. This prior art conducts electricity and detects temperature difference, and, furthermore, requires known-normal and known-abnormal components for finding good components from bad ones, which is quite inconvenient.

Consequently, for detecting wellness of passive routing substrates before stacking, two problems need to be solved: First, the passive routing substrates are passive devices and, therefore, functional tests cannot be run for proving their functional correctness; and, second, the passive routing substrates do not have enough thickness (about 50~100 μm) for detecting their electrical characteristics by probes.

Hence, the prior arts do not fulfill all users' requests on actual use.

SUMMARY OF THE INVENTION

The main purpose of the present invention is to use thermal behavior differences before and after a passive routing substrate is damaged to detect passive routing substrates without contact.

Another purpose of the present invention is to detect passive routing substrates without contacting while a good passive routing substrate is not required in advance for detection.

To achieve the above purposes, the present invention is a device of detecting passive routing substrates without contacting, comprising a heater, an image capture device, a plurality of noise filters, a plurality of differential filters and a comparison module, where the heater heats up a plurality of passive routing substrates; the image capture device is connected with the heater to sequentially capture a thermal image of each of the passive routing substrates to display temperature distribution of the thermal image with different colors; the noise filters are connected with the image capture device to filter noise of the thermal images of the passive routing substrates; the differential filters are connected with the noise filters and every neighboring two of the differential filters compare corresponding neighboring two of the thermal images to obtain thermal behavior changing points in between for obtaining a thermal behavior difference image; the comparison module is connected with the differential filters; the comparison module receives the thermal behavior difference images; the comparison module comprises a first comparator and a second comparator connected with the first comparator; the first comparator compares at least two of the thermal behavior difference images to obtain a good passive routing substrate according to distribution of the thermal behavior changing points of the at least two thermal behavior difference images; and the second comparator compares the thermal behavior difference image of the good passive routing substrate with each of the other thermal behavior difference images to estimate a yield of the passive routing substrates. Accordingly, a novel device of detecting passive routing substrates without contacting is obtained.

BRIEF DESCRIPTION OF THE DRAWINGS

The present invention will be better understood from the following detailed description of the preferred embodiment according to the present invention, taken in conjunction with the accompanying drawings, in which.

DESCRIPTION OF THE PREFERRED EMBODIMENT

The following description of the preferred embodiment is provided to understand the features and the structures of the present invention.

Figure 1:
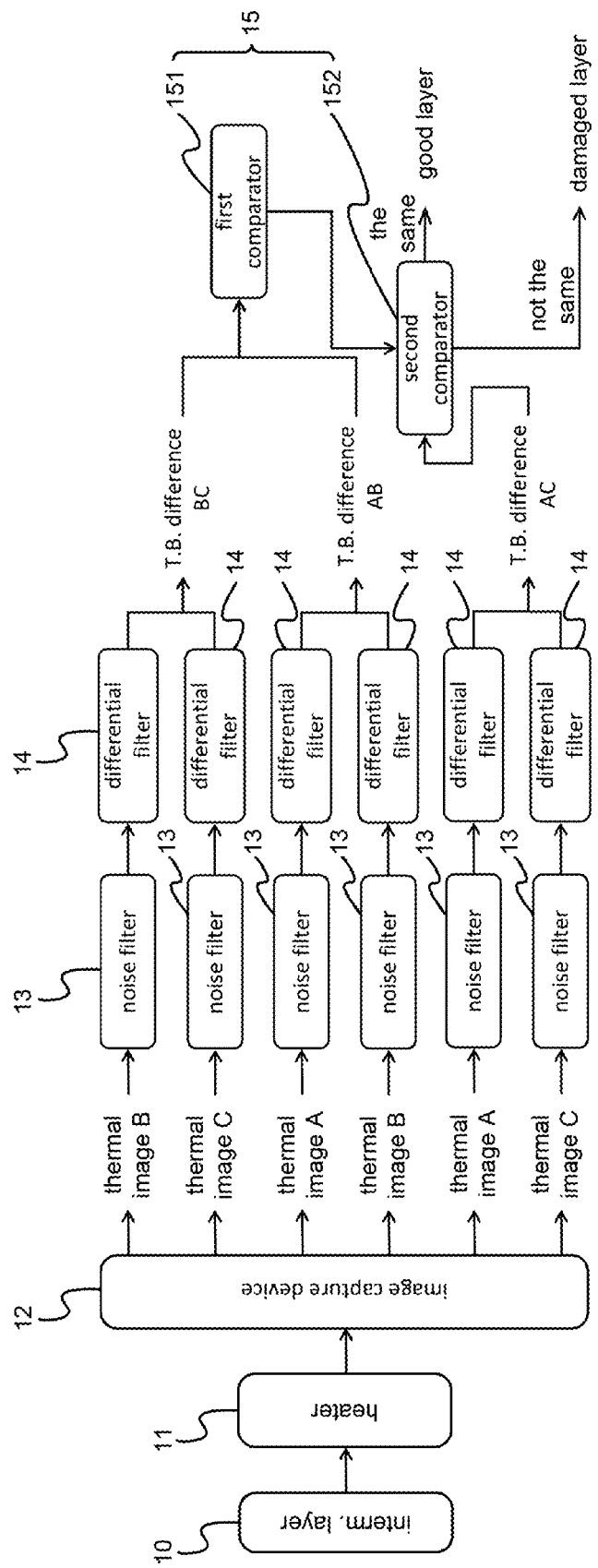
FIG. 1 is the view showing the preferred embodiment according to the present invention.
Figure 2:
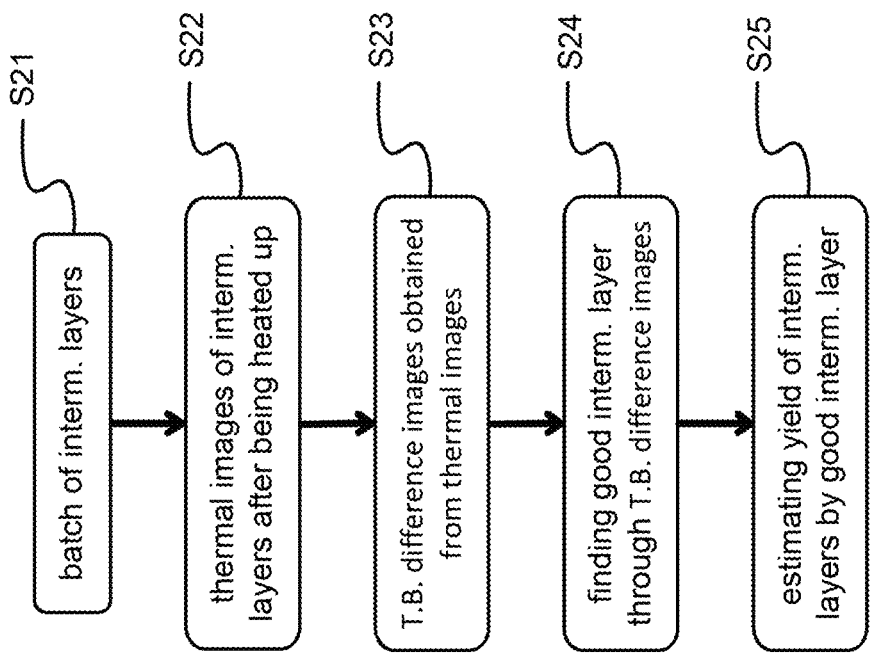
FIG. 2 is the flow view showing the method of the preferred embodiment.
Figure 3:
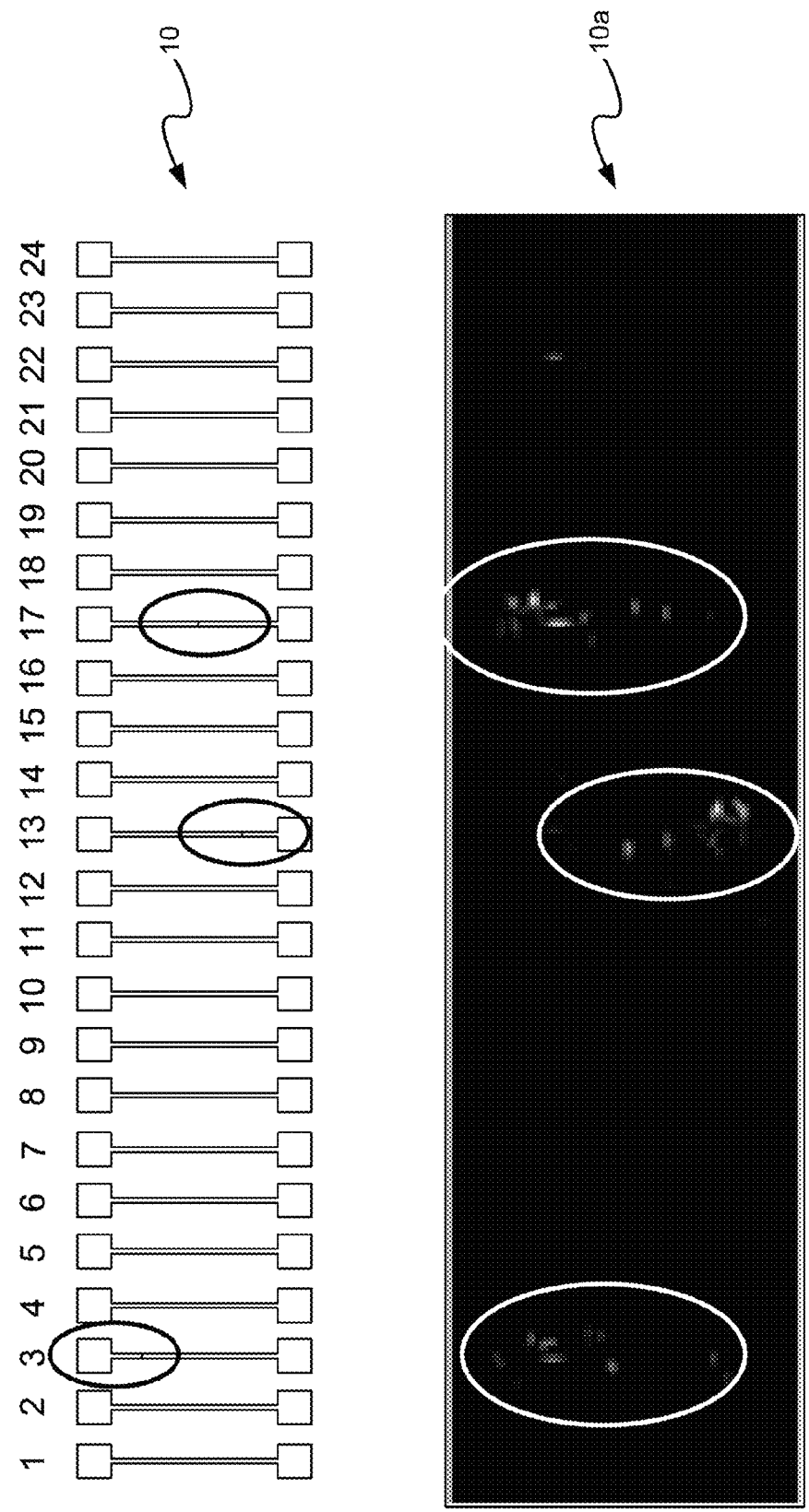
FIG. 3 is the view showing the combined image of the thermal behavior difference images of the good and damaged passive routing substrates.

Please refer to FIG. 1 to FIG. 3, which are a view showing a preferred embodiment according to the present invention; a flow view showing a method of the preferred embodiment; and a view showing a combined image of thermal behavior difference images of good and damaged passive routing substrates. As shown in the figures, the present invention is a device of detecting passive routing substrates without contacting, comprising a heater 11, an image capture device 12, a plurality of noise filters 13, a plurality of differential filters 14 and a comparison module 15.

The heater 11 is an infrared-ray (IR) heater. The image capture device 12, which can be a thermal imager, is connected with the heater 11 to sequentially capture a thermal image of each of a plurality of passive routing substrates for displaying temperature distribution of the thermal image with different colors.

The noise filters 13 are connected with the image capture device 12, where each noise filter 13 receives one of the thermal image to filter noise for obtaining a noise-filtered thermal image.

The differential filters 14 are connected with the noise filters 13 to receive the noise-filtered thermal images correspondingly, where every two neighboring differential filters compares neighboring two of the thermal images to obtain thermal behavior changing points in between for obtaining a thermal behavior difference image of the two thermal images.

The comparison module 15 is connected with the differential filter 14, which comprises a first comparator 151; and a second comparator 152 connected with the first comparator 151.

Thus, a novel device of detecting passive routing substrates without contacting is obtained.

On using the present invention as shown in FIG. 2, the passive routing substrates 10 are provided in step S21, where the passive routing substrates 10 are made of a plurality materials. In step S22, the heater 11 heats up the passive routing substrates 10 for sequentially capturing a corresponding thermal image of each of the passive routing substrates 10 (e.g. thermal image A, B and C) with the coordination of the image capture device 12, where the thermal image displays thermal distribution with different colors. In step S23, the noise filters 13 filter noise of the thermal images to obtain noise-filtered thermal images. Then, the differential filters 14 are used, where every two differential filters 14 compare corresponding two of the thermal images to obtain thermal behavior changing points in between for generating a thermal behavior difference image through fetching a thermal behavior difference (e.g. thermal behavior difference BC, AB, AC) between the corresponding two thermal images. In FIG. 3, a combined image 10a of a plurality of the thermal behavior difference images is obtained through fetching the thermal behavior differences from all of thermal images. In step S24 and step S25, the comparison module 15 receives the thermal behavior difference images to compare at least two of the thermal behavior difference images by the first comparator 151 for finding a good passive routing substrate according to the thermal behavior difference; and, then, the second comparator 152 compares the thermal behavior difference image of the good passive routing substrate with the other thermal behavior difference images to estimate a yield of the passive routing substrates.

A sample of good passive routing substrate is obtained to show damage states of passive routing substrates, where N means no damage. In Table 1, set C of samples is a set of to-be-tested passive routing substrates 10 as shown in FIG. 3. By observing the combined image 10a of the thermal behavior difference images, No. 3, 13 and 17 are found to be damaged.

TABLE 1

|  | Set of samples | | | | |
|---|---|---|---|---|---|
|  | A | B | C | D | E |
| Damaged | N | N | 3<br>13<br>17 | 10 | 6<br>19 |

A few sets of passive routing substrate samples are obtained in advance for experiments, where set A and set B are sets of good passive routing substrates and set C, set D and set E are sets containing damaged passive routing substrates. By using the present invention, these sets of passive routing substrates are detected. In Table 2, the results of the experiments show 100% correctness as expected, which prove the effectiveness of the present invention on detecting passive routing substrates before stacking them.

TABLE 2

|  | Known states | | Results | | |
|---|---|---|---|---|---|
| Experiments | Good | Damaged | Good | Damaged | Correctness |
| Exp. 1 | A | C, D | A | C, D | 100% |
| Exp. 2 | B, | C, E | B, | C, E | 100% |
| Exp. 3 | A, B | C, E | A, B | C, E | 100% |
| Exp. 4 | A, B | C, D, E | A, B | C, D, E | 100% |

The present invention uses thermal behavior difference before and after an passive routing substrate is damaged to detect passive routing substrates without contacting. The present invention heats up the passive routing substrates and capturing their thermal images for obtaining thermal behavior differences in between for finding out good passive routing substrates. Thus, the present invention processes superior and precise detection before stacking the passive routing substrates.

To sum up, the present invention is a device of detecting passive routing substrates without contacting, where thermal behavior difference before and after an passive routing substrate is damaged is used for superior and precise non-contacting detection of passive routing substrates before stacking them.

The preferred embodiment herein disclosed is not intended to unnecessarily limit the scope of the invention. Therefore, simple modifications or variations belonging to the equivalent of the scope of the claims and the instructions disclosed herein for a patent are all within the scope of the present invention.

What is claimed is:

1. A device for fault detecting passive routing substrates without contacting the substrates, comprising a heater, said heater heating up a plurality of passive routing substrates;

an image capture device connected with said heater and sequentially capturing a thermal image of each of said passive routing substrates to display temperature distribution of each said thermal image with different colors;

a plurality of noise filters connected with said image capture device and separately filtering noise of said thermal images of said passive routing substrates;

a plurality of differential filters connected with said noise filters, wherein every two neighboring differential filters compare corresponding neighboring two of said thermal images to obtain thermal behavior changing points in between to obtain a thermal behavior difference image of said two of said thermal images; and a comparison module connected with said differential filters and receiving said thermal behavior difference images, said comparison module comprising a first comparator and a second comparator connected with said first comparator, said first comparator comparing at least two of said thermal behavior difference images to obtain a good passive routing substrate according to distribution of said thermal behavior changing points between said at least two of said thermal behavior difference images, said second comparator comparing said thermal behavior difference image of said good passive routing substrate with each of the other ones of said thermal behavior difference images to estimate a yield of said passive routing substrates.

2. The device according to claim 1, wherein said heater is an infrared-radiation (IR) heater.

* * * * *